(12) United States Patent
Horchover

(10) Patent No.: US 9,615,963 B2
(45) Date of Patent: Apr. 11, 2017

(54) METHOD AND APPARATUS FOR DIAGNOSING SLEEP APNEA

(76) Inventor: Robert L. Horchover, Seattle, WA (US)

( * ) Notice: Subject to any disclaimer, the term of this patent is extended or adjusted under 35 U.S.C. 154(b) by 339 days.

(21) Appl. No.: 13/524,978

(22) Filed: Jun. 15, 2012

(65) Prior Publication Data

US 2012/0247486 A1    Oct. 4, 2012

Related U.S. Application Data

(62) Division of application No. 12/476,872, filed on Jun. 2, 2009, now abandoned.

(51) Int. Cl.
    *A61F 5/56*    (2006.01)
(52) U.S. Cl.
    CPC ..................... *A61F 5/56* (2013.01)
(58) Field of Classification Search
    CPC ...................................... A61F 5/566

USPC ........ 128/848, 846, 857, 859, 861; 433/3, 4, 433/72, 141, 147, 229

See application file for complete search history.

(56) References Cited

U.S. PATENT DOCUMENTS

| | | | |
|---|---|---|---|
| 1,800,714 A | 4/1931 | Clapp | |
| RE23,442 E | 11/1990 | George | |
| 4,997,368 A * | 3/1991 | Mayer et al. | 433/72 |
| 5,154,609 A | 10/1992 | George | |
| 6,055,986 A * | 5/2000 | Meade | 128/848 |
| 6,513,254 B1 * | 2/2003 | Lunn | 33/513 |
| 7,007,697 B1 * | 3/2006 | Della Grotta | 128/848 |
| 2007/0068534 A1 | 3/2007 | Bailey et al. | |

* cited by examiner

*Primary Examiner* — Tarla Patel

(57) ABSTRACT

A method and apparatus for diagnosing sleep apnea and for comfortably fitting an oral device to treat the condition. The patient is screened to reduce snoring using a device which changes the airway, and then using an airway dilation simulator having sequentially sized elements to determine the mandibular position maximizing the upper airway dimension. An oral device is then fabricated to retain the maximum position during sleep.

6 Claims, 3 Drawing Sheets

METHOD AND APPARATUS FOR DIAGNOSING SLEEP APNEA

This application is a divisional application of U.S. application Ser. No. 12/476,872 filed on Jun. 2, 2009, now abandoned.

TECHNICAL FIELD

This invention relates to sleep apnea, and more particularly, to an apparatus for diagnosing and treating sleep apnea, including the method of measuring the airway with the mandible in precisely displaced positions until the airway allows a maximum airflow within the comfort zone of the patient, and then fabricating an appliance to maintain the mandibular position during sleep.

BACKGROUND OF THE INVENTION

Although sleep apnea has been recognized as a critical life-endangering problem, there are still a limited number of doctors or dentists trained to treat this disorder and a limited number of treatments. The traditional options for treating obstructive sleep apnea, which is a medical condition where there is a blockage of the airway usually caused by the soft tissue in the rear of the throat, which collapses and closes during sleep, are with the nasal continuous positive air pressure (nCPAP), an oral airway dilator or with surgery. The treatments using positive air pressure and the oral airway dilators (OAD) are not cures, but reversible management tools.

Some of the common design features in the first generation (OADs) airway dilator resulted in minimal success and gave them a negative image in sleep medicine. The current designs of the OADs have increased their successes, and they are now more widely accepted for managing sleep apnea and are far more user-friendly and socially acceptable.

The current CPAPs on the market are expensive, difficult to adjust and largely uncomfortable, and therefore disagreeable to the patient during the diagnosis and fitting process. Further, a percentage of these devices are non-compliant.

Current publications which are not necessarily directly related to sleep apnea but may be considered prior art to the current invention include:

U.S. Pat. No. 1,800,714 granted to Clapp Apr. 14, 1931, which discloses a stepped device for determining the particular bite when artificial dentures are needed, and the device includes a scale intended to measure the angle of a line drawn from the crest of the upper edentulous ridge to the crest of the lower edentulous ridge.

U.S. Pat. No. Re 23,442 granted to George Nov. 20, 1990, teaches the use of an appliance designed to prevent the occlusion of the oro-pharngeal airway, which includes a front beak.

U.S. Pat. No. 4,997,368 granted to Mayer et al Mar. 5, 1991, discloses an oral measuring device for determining the size of the mouth opening and the range of motion to determine the success or nature of the operation performed following facial or oral surgery.

U.S. Pat. No. 5,154,609 granted to George Oct. 15, 1992, discloses an instrument including calibrations and extensions for registration of the dental bite of a patient, and includes as a combination a bite fork.

DISCLOSURE OF THE INVENTION

With the above-noted prior art and inadequacies in mind, it is the goal of the present invention to provide a simple, straightforward diagnostic tool for obstructive sleep apnea, as well as a simple, accurate tool for determining the optimal position of the mandibular to maximize the air flow while not compromising the comfort of the patient. The diagnostic tool allows the dental personnel to quickly measure the position of the patient's lower jaw when maximizing the air flow to determine the suitability of the possible use of an oral airway dilator.

The airway dilution simulator comprises a plurality of sequentially sized elements for positioning the mandible as guided by the patients' subjective feedback on their airway changes and comfort. The utilization of the present invention also quickly interfaces with acoustic reflection pharyngometry that measures the upper airway dimension in any of the mandibular positions with this invention, thus permitting the dental personnel to determine the position for maximum air flow.

Following the determination of maximum airway dimension, the dental personnel can fabricate an oral device to retain the mandible in the optimal position during sleep. The process of achieving the optimal position of the mandible may take more than one measurement and more than one adjustment, spread out over a period of time, to allow the patient to comfortably adjust to the proscribed changes.

BEST MODE FOR CARRYING OUT THE INVENTION

Figure 1:
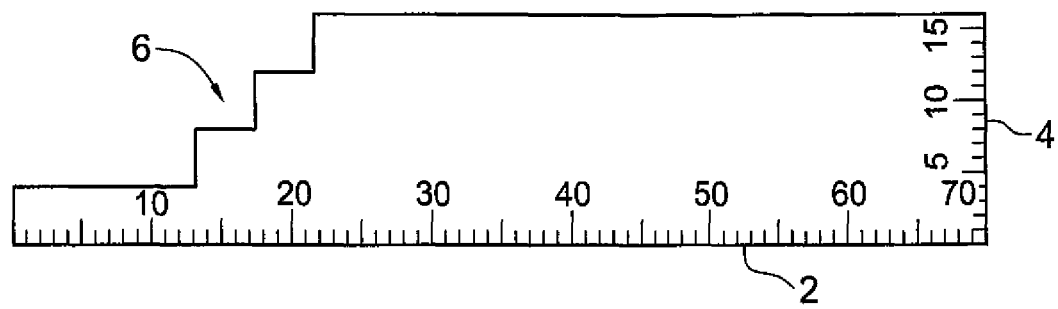
FIG. 1 is an elevational view of the snoring/airway screener.

As seen in FIG. 1, the snoring/airway screener which empirically utilizes the snoring sound generated by the patient and is relatively low tech, but empirically shows a high correlation with the airway size in the airway segment that obstructive sleep apnea airway dilators falter. Therefore, it is an effective screening tool. The screener serves as a quick way to narrow the more definitive analysis zone for optimum airway flow. The system enables repeatability in any position.

Historically, after the standard muscle joint and range of motion screening, there were no devices or accepted techniques for predicting success with an oral airway dilator. Sonar technology has been adapted to measure the upper airway by sending an echo through the mouth and into the airway while the patient holds a snorkel-like mouthpiece between their teeth and breathes naturally. This process is actually comfortable, cost-effective and also produces data and graphical output for analysis. This modality is called acoustic reflective phargynometry, where the instrument effectively measures the status quo of the patient but nothing exists to show the phargynometry to simulate jaw positions to determine whether they are a candidate for the oral airway dilator treatment and which device would be more effective.

The snoring/airway screener as shown in FIG. 1, as noted hereinabove, is an effective screening tool for detecting airway dilator candidacy, having a high correlation with a pharyngometer. The device itself is a relatively thin piece of material which is sterilizable, having a bottom surface 2 calibrated, a rear surface 4 likewise calibrated, and a front surface 6 of a stair-step design, such that in use, the patient places his upper incisor on the desired step (as designated by the calibration) and moves the lower jaw to the position wherein the snore noise is least, giving the clinician the quick determination and accurate location indicating that this type of correction could and would be useful as a reference for further treatment and perhaps installation of an oral airway dilator.

Figure 2:
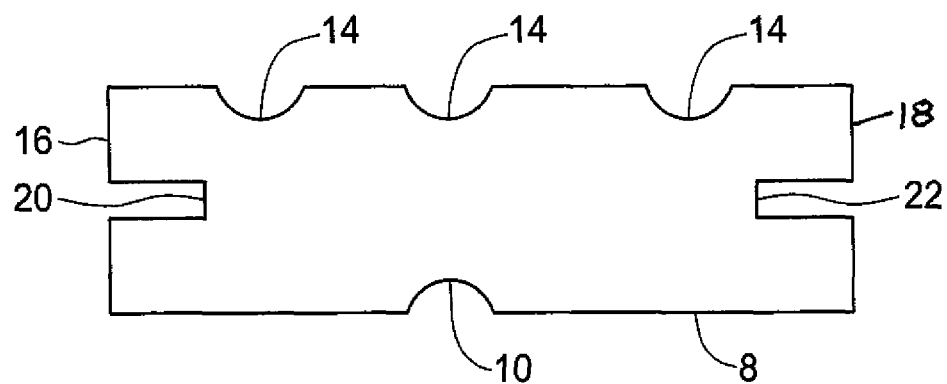
FIG. 2 is a side elevational view of one of a series of airway dilation simulators.

As seen in FIG. 2, one of the airway dilation simulators is shown. It comprises a relatively thin piece of material which is sterilizable and, as explained hereinafter, is shown as only one of a series of simulators that are used to allow the pharyngometer testing of the jaw and airway dimension in simulated positions. The simulator is a rectangular piece of material having a bottom 8, including an indentation or notch 10 for the lower incisor, a top 12 having one or more indentations or notches 14 for the placement of the upper incisor to selectively find the maximum air flow position through the sequential use of the graduated set until the clinician determines which relative position maximizes the flow and least comprises comfort. The mandibular positioning simulator includes inscribed information telling the clinician precisely the relative location, vertical and horizontal, of the incisors to reduce the chance of error and permitting an accurate repetition of positions. The simulator includes two end portions 16 and 18, each including a slot 20-22 for reasons to be explained hereinafter.

Figure 3:
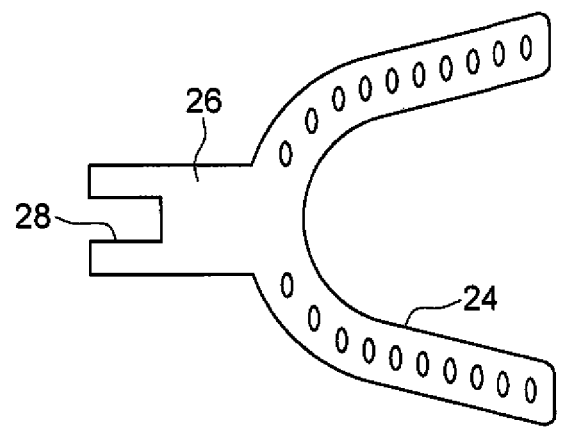
FIG. 3 is a plan view of the bite fork.

Reference is now had to FIG. 3, wherein an instrument, generally known as a bite fork, is shown, which includes a horseshoe-shaped main body portion 24 having a plurality of spaced openings, and a rearwardly projecting mounting member 26 having an inwardly projecting slot 28.

Figure 4:
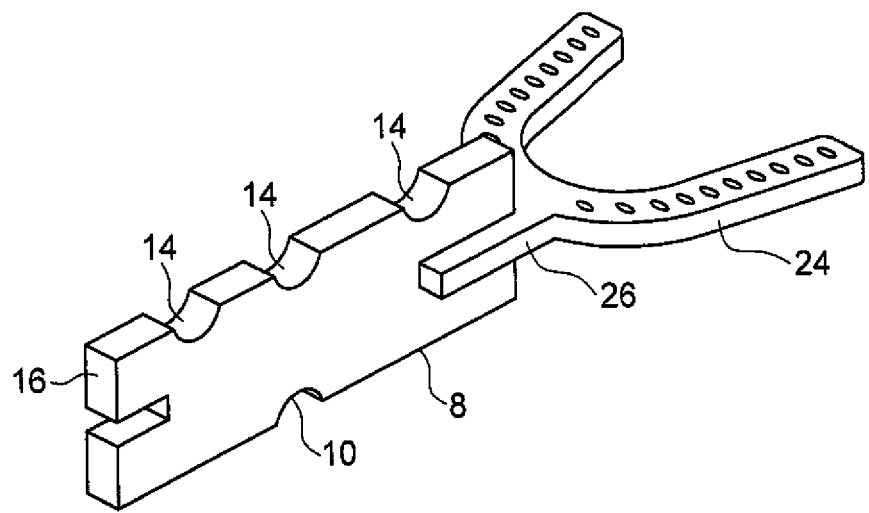
FIG. 4 is an illustration of the portion of a set of a series of the airway dilation simulator as seen in FIG. 2.

As seen in FIG. 4, the simulator as shown in FIG. 2 is shown in conjunction with the fork of FIG. 3, such that when the optimal relative jaw position both vertical and horizontal is determined using the simulator and the pharyngometer, then the fork is attached to the simulator. This provides the correct jaw position and a fitting substance is spread evenly on the fork so that the impression of the patient's teeth can be reproduced in the oral airway dilator, which is fabricated using the information achieved through the combination of the pharyngometer and the sequential use of the simulators.

Figure 5:
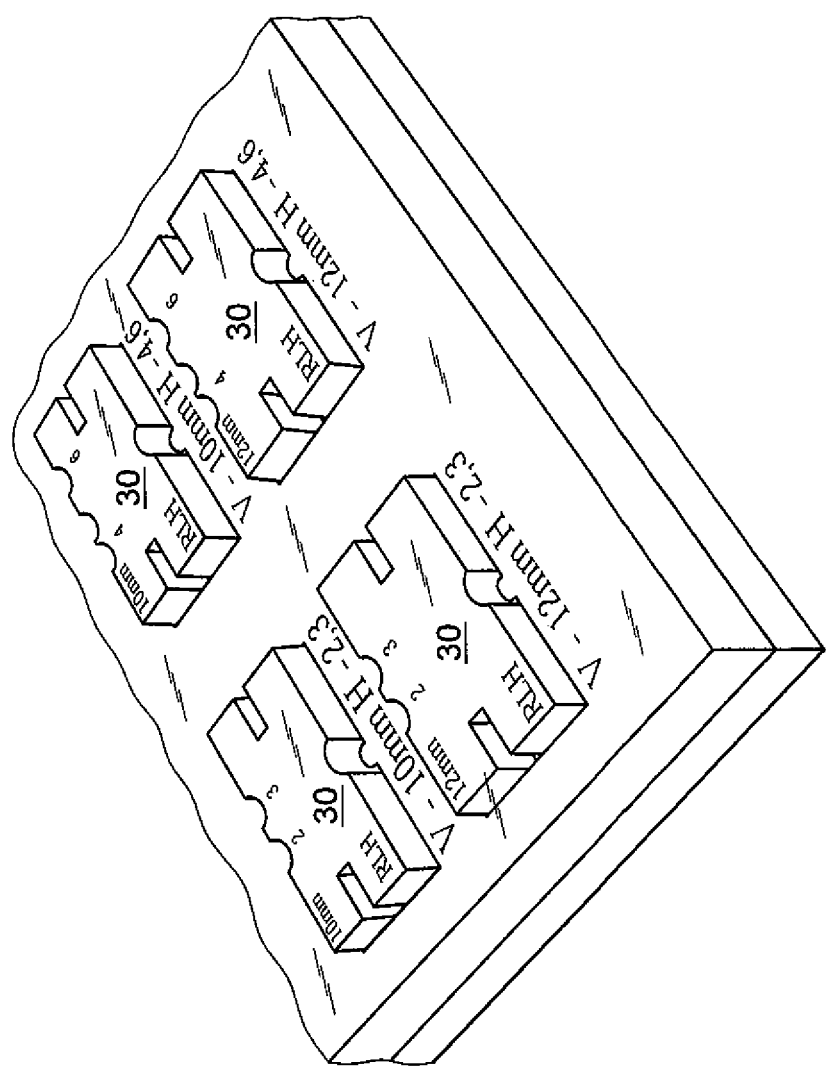
FIG. 5 is an illustration of a kit of dilation simulators.

Reference is now had to FIG. 5, wherein there is shown a portion of a kit, including a plurality of the simulators 30, 15 in a case. It is important to note that the simulators vary in height from 4 mm to 12 mm and the horizontal displacement of the lower mandible varies from 2 mm to 7 mm, allowing the clinician to place a series of the simulator in the mouth of the patient with or without the pharyngometer to determine the maximum and minimum discomfort as plotted on a graph. It is to be understood that the simulators are constructed such that they can be reversed as desired, thereby providing over 50 selected jaw positions.

Thus, as can be seen, the present invention provides a quick and simple, straightforward method and apparatus for a snoring/airway screener and a kit which allows the clinician to use the pharyngometer to determine airway dimensions, predicting air flow while noting the precise position, horizontally and vertically, of the mandibles.

Mandibular positioning system for optimum airway includes fifteen simulators which provide 40 horizontal and vertical combinations that enable bite registration in the selected position. Simulators, easily placed by patient, create simple, effective, repeatable, and predictable position for device effectiveness and quickly interface with pharyngometry. Accessories enable screening and device tuning.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. A kit for determining and simulating the optimal airway dilation by adjusting jaw position for a person having obstructive sleep apnea, comprising a plurality of similar discrete rectangular elements having different height dimensions, having ends, a thickness and sides, wherein each element includes opposing slots extending inwardly from the ends, each element further contains a notch mid-point on one side and at least two notches on the opposite side, said notches determining a jaw position in a horizontal plane when a person's incisors are placed in the notches, said elements further having predetermined end dimensions to control the jaw position in a vertical plane.

2. A diagnostic kit for determining and simulating a person's optimal airway dilation in cooperation with the person, having jaws and teeth, by manipulating juxtaposition of upper and lower jaws by engaging the teeth, comprising a pair of related devices, a first elongated, rectangular screening device having an upper and a lower surface including a stepped portion on one end to engage upper front teeth and a smooth graduated lower surface to note protrusion of a person's mandible defining maximum airflow and a starting position to be refined using a second device, which comprises a plurality of rectangular discrete elements, having a thickness of graduated height dimensions including one notch on the lower surface and at least two notches on the upper surface for engaging the teeth, enabling a quick interchange of discrete elements for a person's subjective assessment of comfort at varying positions near the starting position.

3. A kit as in claim 2, wherein the second device includes multiple elements.

4. A kit as in claim 2, wherein the discrete elements are compatible with a pharyngometer.

5. A set of tools for diagnosing breathing disorders by determining an optimal horizontal and vertical position of a person's incisors to maximize airflow, including a set of discrete airway dilation simulators, including positioning notches therein to receive the upper and lower incisors controlling relative vertical and horizontal positions of the person's incisors, enabling comparative airway measurements, wherein the simulators are thin and are compatible with and allow pharyngometer testing of a person's jaw and airway dimension in simulated positions when the airway dilation simulators and the pharyngometer are in place in a person's mouth; wherein the airway dilation simulators include slots extending inwardly from opposing ends thereof.

6. The set of tools of claim 5, including in combination therewith a bite fork which includes a horseshoe shaped main body portion with a plurality of spaced openings and a projecting mounting member having an inwardly projecting slot adapted to mate with a corresponding slot in a dilation simulator.

* * * * *